United States Patent [19]
Kavteladze et al.

[11] Patent Number: 5,683,411
[45] Date of Patent: Nov. 4, 1997

[54] MEDICAL ARTICLE FOR IMPLANTATION INTO THE VASCULAR SYSTEM OF A PATIENT

[75] Inventors: Zaza A. Kavteladze; Aleksandr P. Korshok, both of Moscow, Russian Federation

[73] Assignee: William Cook Europe A/S, Bjaeverskov, Denmark

[21] Appl. No.: 464,698

[22] PCT Filed: Apr. 6, 1995

[86] PCT No.: PCT/DK95/00147

§ 371 Date: Jun. 7, 1995

§ 102(e) Date: Jun. 7, 1995

[87] PCT Pub. No.: WO95/27448

PCT Pub. Date: Oct. 19, 1995

[30] Foreign Application Priority Data

Apr. 6, 1994 [RU] Russian Federation ............ 94012016
Apr. 19, 1994 [RU] Russian Federation ............ 94014593

[51] Int. Cl.$^6$ .................. A61M 29/00; A61F 2/04
[52] U.S. Cl. .................. 606/200; 623/11; 623/12
[58] Field of Search ................ 606/200, 191, 606/194, 198; 623/1, 11, 12

[56] References Cited

U.S. PATENT DOCUMENTS

| | | |
|---|---|---|
| 3,874,388 | 4/1975 | King et al. . |
| 4,007,743 | 2/1977 | Blake . |
| 4,619,246 | 10/1986 | Molgaard-Nielsen et al. ......... 606/200 |
| 4,643,184 | 2/1987 | Mobin-Uddin ........................... 606/200 |
| 4,817,600 | 4/1989 | Herms et al. ........................... 606/200 |
| 4,832,055 | 5/1989 | Palestant ................................. 606/200 |
| 5,059,205 | 10/1991 | El-Nounou et al. .................... 606/200 |
| 5,064,435 | 11/1991 | Porter ..................................... 623/12 |

FOREIGN PATENT DOCUMENTS

| | | |
|---|---|---|
| 0587197 | 3/1994 | European Pat. Off. . |
| 2567405 | 1/1986 | France . |
| 810246 | 3/1981 | U.S.S.R. . |
| 9310714 | 6/1993 | WIPO . |
| 9412136 | 6/1994 | WIPO . |

OTHER PUBLICATIONS

Frasson, F. et al.,"Embolization of renal Tumors," *Ann. Radiology*, 1981, vol. 24, No. 5, pp. 396–398.

Rashkind, W.J. et al., "Nonsurgical closure of patent ductus arteriosus: clinical application of the Rashkind PDA Occluder System," *Circulation*, vol. 75, No. 3, Mar. 1987, pp. 583–592.

Günther, Rolf. W., et al., "Vena Caval Filter to Prevent Pulmonary Embolism: Experimental Study," *Radiology*, Aug. 1995, vol. 156, No. 2, pp. 315–320.

*Primary Examiner*—Michael Buiz
*Assistant Examiner*—Patrick W. Rasche
*Attorney, Agent, or Firm*—Richard J. Godlewski

[57] ABSTRACT

A medical article for implantation into the vascular system of a patient comprises a self expanding body shaped substantially into the form of a body (1; 2) of revolution, at least part of the surface of which is defined by wire members (3) forming cells of a generally polygonal shape. The body of revolution has a diameter increasing continuously in an axial direction of the body from one end forming an apex (4) towards the opposite end forming a base (5). In a preferred embodiment, the body (1; 2) of revolution is defined by a generatrix forming n-th order curve. The article may comprise two bodies (1; 2) of revolution joined at their apices (4). The article may be used, in particular as an intravenous filter for the capture of thrombi or in combination with an elastic blood impermeable membrane flexibly linked to the apex of the body of revolution as an occlusion device for closing a vessel lumen or defects such as ASD or PDA in vascular walls.

13 Claims, 5 Drawing Sheets

MEDICAL ARTICLE FOR IMPLANTATION INTO THE VASCULAR SYSTEM OF A PATIENT

This application is a 371 of PCT/DK95/00147 filed Jun. 4, 1995.

The invention relates to a medical article for implantation into the vascular system of a patient, comprising a self expanding body shaped substantially into the form of a body of revolution, the surface of which is defined by wire members forming cells of a generally polygonal shape over at least a part of said surface.

Medical implantation articles to which the invention pertains have found wide-spread use in percutaneous vascular and cardiac surgery and comprise in particular intravenous filter devices for the capture of thrombi in major veins such as the lower caval vein and occlusion devices for permanent or temporary obturation of a vessel lumen or permanent occlusion of defects in vascular walls such as an ASD (atrial septal defect) in the atrial septum, a PDA (Patent Ductus Arteriosus) defect or other defects in vascular walls such as the inlet of an exfoliative aneurism of the aorta or a puncture hole in connection with angiographic investigation.

Intravenous filters for capture of thrombi have become known in many different configurations and shapes.

FR-A-2567407 discloses an umbrella-type filter comprising a number of radial legs interconnected at their ends by a semi-spherical filter membrane permeable to the blood flow.

This prior art device requires a comparatively large diameter delivery system involving a considerable risk for traumatization of the femoral or subclavian veins used for percutaneous introduction. Correct localization in the caval vein is rather difficult and unreliable and a further drawback follows from the impossibility of withdrawing the filter in cases where such withdrawal is dictated by a clinical indication.

From Radiology, 1985, 156, pages 315 to 320 a filter in the form of the body of revolution made from wire members forming a cellular surface is known. This prior art device suffers from the drawback that captured thrombi will tend to collect in the peripheral or parietal zone of the filter, whereby the efficiency of operation is impaired. Also for this prior art filter a considerable risk for traumatization of vessels during introduction prevails and it is not possible to withdraw the filter.

Also medical articles of the kind referred to for occlusion of vessels or holes in vascular walls have become known in different configurations and shapes.

From Ann.Radiology, 1981, vol. 24, no. 5, pages 396 to 399 a vessel occlusion device is known having the shape of a spring spiral. With this device it has turned out to be difficult and complicated to obtain full and effective closing of a vessel lumen and the device suffers moreover from the drawback of a significant risk of displacement from the site of implantation due to blood flow or pulsation of vascular walls.

A prior art occlusion device known from SU inventors certificate No. 810246 comprises a body of revolution formed by an inflated balloon with a catheter. For this device non-uniform inflation of the balloon will result in insufficient sealing of the body against the vascular walls adjoining the duct to be closed and the occlusion will be of a rather poor quality and ineffective.

Further prior art occlusion devices for sealing cardiovascular defects comprise the shunt defect closure devices disclosed in U.S. Pat. Nos. 3,874,388 and 4,007,743. Both of these prior art devices comprise a pair of umbrella-like elements, which only after localization at the site of the defect are locked together in face to face relationship to close the defect from opposite sides.

In an article "Non-surgical closure of patent ductus arteriosus: Clinical Application of the Rashkind PDA occluder system", circulation 75 No. 3, March 1987 an occluder system is described comprising two polyurethane discs mounted on two opposing umbrella-like three-armed spring assemblies. Whereas the need for assembling the two assemblies after installation has in this case been avoided this has been obtained at the expense of a rather complicated delivery system and procedure.

A similar drawback in addition to a rather complicated structure of the occlusion device itself prevail with a prior art ASD and PDA occluder device dissolved in international patent application WO 93/10714.

On the background of the prior art described above it is the object of the invention to provide a medical implantation article of the kind defined which does not suffer from the above-mentioned drawbacks of the prior art and is equally applicable for use as an intravenous filter device for arrangement in a major vein such as the lower caval vein and as supporting structure of an occlusion device for closing a vessel lumen or defects in vascular walls as mentioned above.

According to the invention, this object is achieved by providing a medical article for implantation into the vascular system of a patient as defined hereinbefore, which is characterized in that said body of revolution has a diameter increasing continuously in an axial direction of the body from one end forming an apex towards the opposite end forming a base.

When used as an intravenous filter the medical article of the invention will be arranged in the actual vein with such an orientation of the body of revolution that the apical end thereof will be directed downstream of the blood flow. Thereby, the thrombotic masses will be collected in the center of the lumen of the vein so that the filtration efficiency is enhanced. Correct localization of such a filter device may be secured with great reliability by dimensioning the diameter of the base of the body of revolution to be larger than that of the vessel, whereby also an increased versatility is achieved in the sense that for a specific vein such as the lower caval vein one and the same filter size can be used with any possible diameter of the vessel.

According to a preferred embodiment the body of revolution of the medical article of the invention is defined by a generatrix forming a n-th order curve according to the formula $$y = Ax^n$$

where for a given point on the surface of the body x is the radius in the radial plane including said point, y is the distance from said radial plane to a plane parallel thereto including the geometrical apex, A is a constant and $n \geq 1$. Thereby the general shape of the body of revolution may vary from a conical to a more or less pronounced parabolic shape of varying slope as determined by the constant A.

When the medical article of the invention is intended for permanent implantation as an intravenous filter or an occlusion device a reliable localization of the article may be further secured in a manner known per se by the provision of anchoring members for fixing the article to vascular walls at the circumference of the base of the body of revolution.

Due to the shape of the medical article a further advantageous possibility of withdrawing the article, if this is required or recommended by a clinical indication, may be obtained by providing the medical article with wire members extending substantially diametrically across the base of the body of revolution and connected with each other at the centre to function as extraction members, which can be engaged by a hook-shaped trapping wire introduced by means of a retraction catheter.

For use of the medical article of the invention as an occluder device for closing a vessel lumen or defects in vascular walls as mentioned above, a further preferred embodiment of the article is characterized in that an elastic membrane of a blood impermeable material is arranged at one end of said body of revolution and coaxially therewith, said membrane having a diameter exceeding the maximal diameter at the base of said body.

Such a membrane will preferably be arranged at the apical end of the body of revolution and be connected therewith through a flexible link allowing the occluder device including the membrane and the body of revolution to be accommodated and introduced into a vessel by means of a relatively simple introducer catheter with a small external diameter without any need of assembling separate components after localization of the article at the site of installation.

In this design the medical article of the invention will secure reliable and complete obturation of a vessel lumen and provide safe occlusion of defects in vascular walls of any geometry and size and in any anatomic zone of the body.

For both of the above-mentioned applications of the medical article of the invention the article may advantageously comprise two bodies of revolution joined at their apices.

In the following the invention will be further explained with reference to the accompanying drawings in which FIG. 1 is a perspective view of a first embodiment of a medical article according to the invention serving as an intravenous filter device;

Figure 1:
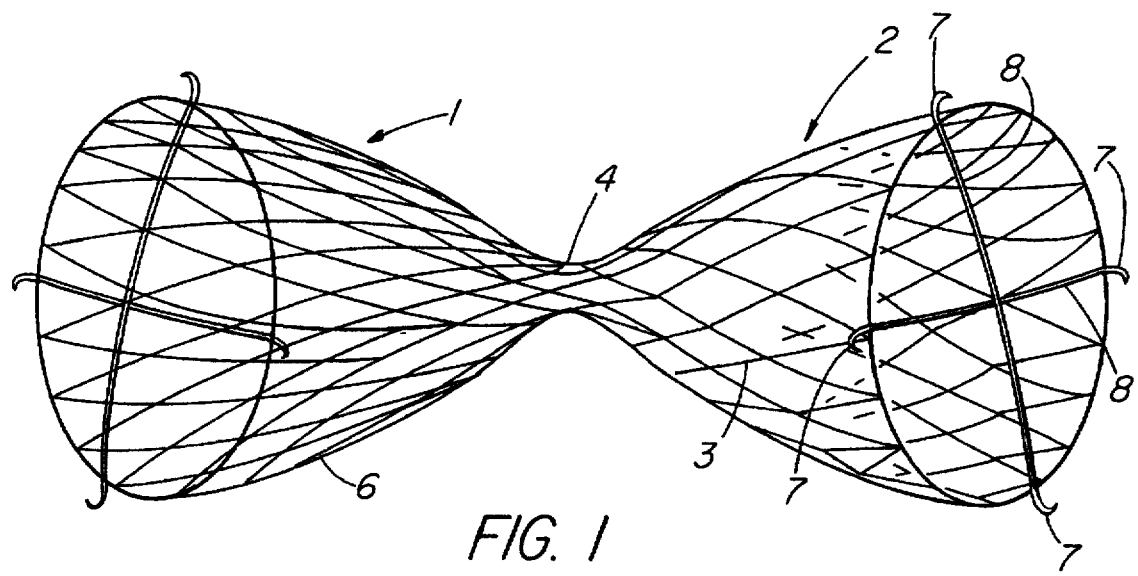

The intravenous filter shown in FIG. 1 comprises two coaxial interconnected bodies of revolution 1 and 2 each defined by wire members 3 forming cells of a general rhombic shape over at least part of the surface of the body of revolution.

According to the invention, each of the bodies of revolution 1 and 2, which are of the same general shape, has a diameter increasing continuously in the axial direction from an apical end 4 towards the opposite end of the respective body which forms a base 5.

Figure 2:
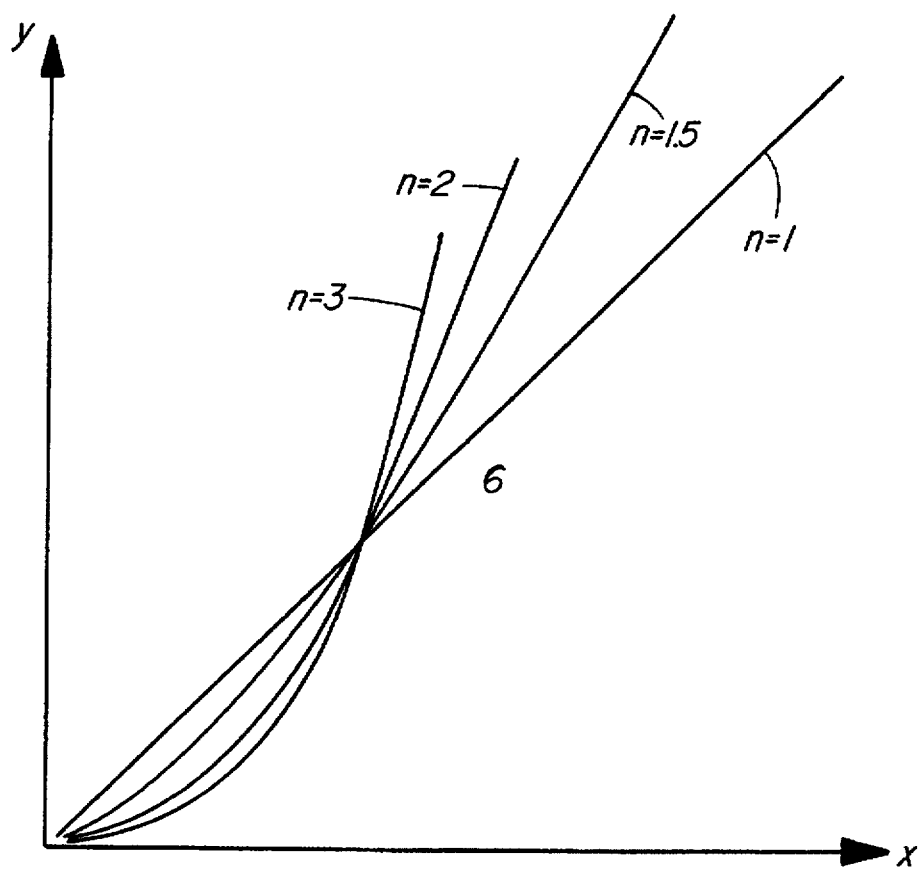
FIG. 2 is a graphic representation by way of example of some possible contours of a body of revolution in a medical article according to the invention.

In the illustrated embodiment each of the bodies of revolution 1 and 2 is defined by a generatrix 6 forming a socalled n-th order curve as further illustrated in FIG. 2. Mathematically this means that the generatrix 6 may be defined by the formula $$y = Ax^n$$

where for given point on the surface of the body of revolution x will represent the radius in the radial plane including said point, whereas y will represent the distance of said radial plane from a plane parallel thereto and including the geometrical apex 4 where the two bodies of revolution 1 and 2 are joining each other; A is a constant the magnitude of which will depend of the actual application and may typically be within the range $0{,}2 \leq a \leq 1$. For the intravenous filter embodiment shown in FIG. 1 A will typically be equal or close to 1.

FIG. 2 illustrates for A=1 the shape of the generatrix curve x for values of the power n ranging from n=1 (straight line) to n=3.

To achieve the object of collecting captured thrombi in the center region of each of bodies 1 and 2 the power factor n may be equal to n=1, whereby the body of revolution will take a generally conical form or it may be within the range $$1 < n \leq 2$$

whereby the body of revolution will assume a more or less pronounced parabolic shape.

For the purpose of reliably fixing of the filter at a site of installation in a vein such as the lower caval vein anchoring members 7 may be provided along the circumference of the base 5.

As a special feature the filter may be provided with wire members 8 extending diametrically across the base 5 of one or both of the bodies of revolution 1 and 2 and being secured to one another at the centre of the base to function as extraction members engageable by a hook-shaped trapping wire introduced into the vein by means of a retraction catheter, not shown.

Due to the cellular surface of each of the bodies of revolution 1 and 2 and the geometrical shape thereof as explained above the entire filter composed of the two bodies of revolution may be stretched in the direction of its axis and arranged in the distal end of a hollow radioopaque introduction catheter of a small external diameter, e.g 2.5 mm, which may be introduced percutaneously into the vascular system of a patient through a paracentetic puncture in a femoral or subclavian vein.

Such a small diameter introduction catheter will cause minimum traumatization of the wails of the vein through which the catheter with the filter is introduced.

At the desired site of implantation, such as in the lower caval vein, the filter is ejected from the introduction catheter by means of a pushing member slidably arranged inside the catheter and, by dimensioning the diameter of the base of each of the bodies of revolution 1 and 2 to be larger than the diameter of the vein or other vessel, reliable localization of the filter may be obtained also in case of temporary implantation where anchoring members are not used.

For permanent installations an even more reliable localization may be obtained by means of the anchoring members 7 provided at the circumference of the base of at least one of the bodies of revolution.

In the illustrated embodiment of the filter with two slightly parabolic bodies of revolution 1 and 2 one of these bodies will form an active filter part having its apex oriented downstream with respect to the blood flow whereby thrombotic masses will be collected at the apex and thus in the center of the lumen of the vein in which the filter is arranged. In the peripheral parts of the lumen a substantially free flow of blood will be ensured. Thereby, the risk of obturation of the vein lumen by thrombotic masses will be significantly reduced.

The filter may also be made of a single body of revolution of a general shape as outlined above.

Figure 3:
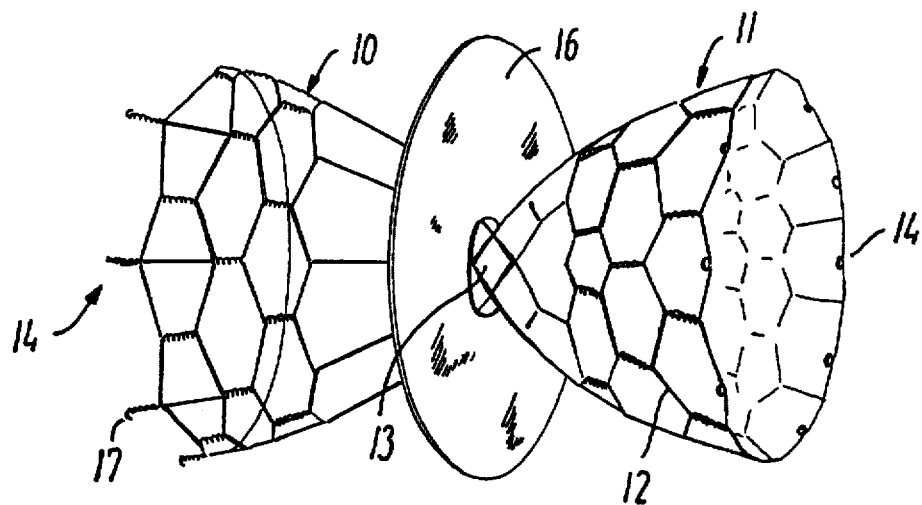
FIGS. 3 to 5 illustrate a second embodiment of the medical article according to the invention serving as an occlusion device, in a perspective view, a side view and an end view, respectively.
Figure 4:
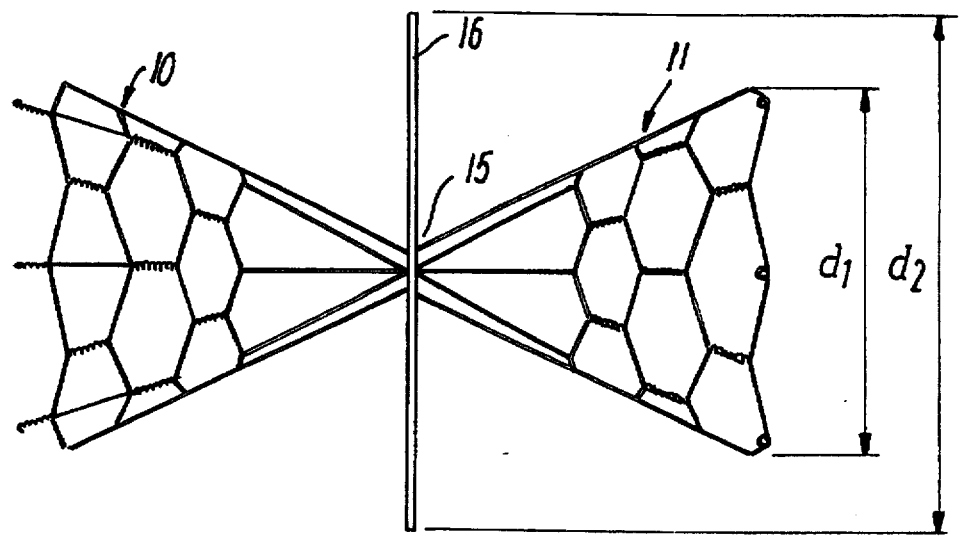
Figure 5:
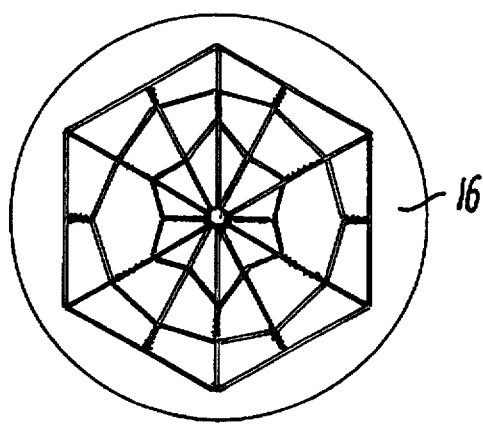

In FIGS. 3 to 5 another embodiment of the medical article of the invention is illustrated which is intended to function as a vessel occlusion device. Also in this embodiment the article is composed of two bodies of revolution 10 and 11 each of which has a general shape as described above and is defined by wire members 12 forming substantially hexagonal cells over at least a part of the surface of the body of revolution.

Thus, the two bodies 10 and 11 may each have a conical or more or less pronounced parabolic shape with a diameter increasing continuously from an apical end 13 towards the opposite end forming a base 14. In the above-mentioned mathematical expression this will correspond to a value of A equal or close to 1 and a value of n in the range $1 \leq n \leq 2$. At their apices 13 the two bodies 10 and 11 are joined and connected by means of a flexible link 15 with an elastic occlusion membrane 16 made of an blood impermeable material. The membrane 16 has a diameter $d_2$ which is at least equal to, but preferably greater than the diameter $d_1$ of the base of each body of revolution.

The blood impermeable elastic membrane 16 may be formed from a porous film or a non-woven fabric of e.g. polyurethane, polyethylene, polyamide or expanded PTFE.

In the same way as in the filter embodiment of FIG. 1 hook-like anchoring members 17 may be provided at base 14 of one or both of the bodies of revolution 10 and 11 to ensure reliable permanent fixing and localization of the occlusion device at a site of implantation.

As described above for the filter embodiment of FIG. 1 the occluder embodiment in FIGS. 3 to 5 may be easily arranged in the distal end of an introduction catheter, not shown, having a fairly small external diameter such as 2.5 mm and may be percutaneously introduced through the venous system or a puncture hole in a vessel segment. After introduction the occlusion device is ejected from the catheter and may completely obturate a vessel lumen due to the elastic membrane 16 which is reliably retained at the site of implantation by the self-expansion of the two bodies of revolution 10 and 11 assisted by the pressure gradient from the blood the flow of which is instantly blocked by the occlusion of the vessel.

Due to its flexibility and the general shape of the bodies of the revolution as well as the cellular surface made up of wire members 12 the occlusion device is very flexible and suitable for introduction by means of an equally flexible conveying system whereby the risk of traumatization may be kept very low and the universality of the occlusion device for implantation in vessels of various diameters and geometry is ensured.

Figures 6, 7:
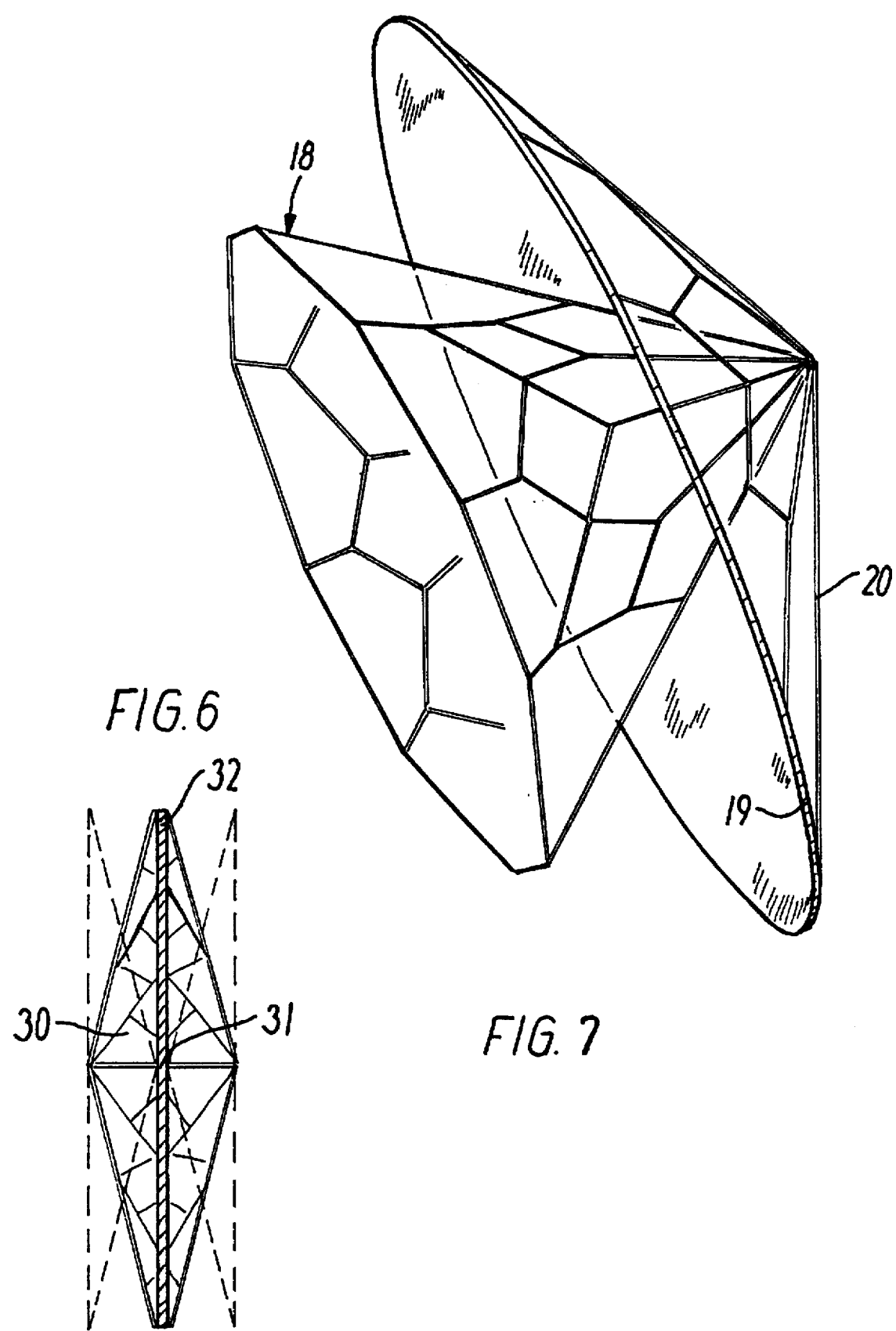
FIGS. 6 and 7 shows alternative embodiment serving as occlusion devices for defects in vascular walls.

In stead of being joined together at their apices the two bodies of revolution 30 may as shown in FIG. 6 have their apices somewhat separated and displaceably connected by a flexible axially extending wire member 31 to which the elastic blood impermeable membrane 32 is fixed. In the state of introduction, the bodies are turned inside out as shown in dotted lines to bring their apical ends into abutment with the membrane 32. After localization at the site of implantation this elastic deformation is reversed to cause the two bodies to be oriented with their bases facing each other and the elastic membrane.

With this modification the occlusion device may be suitable for closing of a socalled ASD-defect i.e. a defect in the atrial septum between the right and left atria. For this application, the conical or parabolic bodies of revolution may typically have a pronounced flat shape corresponding to values of A around 0,2 in the mathematical expression stated above.

FIG. 7 shows a different embodiment of an occlusion device specially intended for curing the fatal condition known as Patent Ductus Arteriosis (PDA) caused by a duct or flow passage between the pulmonary arteria and the aorta. In this embodiment, the device comprises only a single body of revolution 18 which as shown may be of a generally conical shape the apical end of which is connected through a flexible link with the elastic blood impermeable membrane 19 which in this case may be supported on its external side by an umbrella-like structure 20 of wire members.

Figure 8:
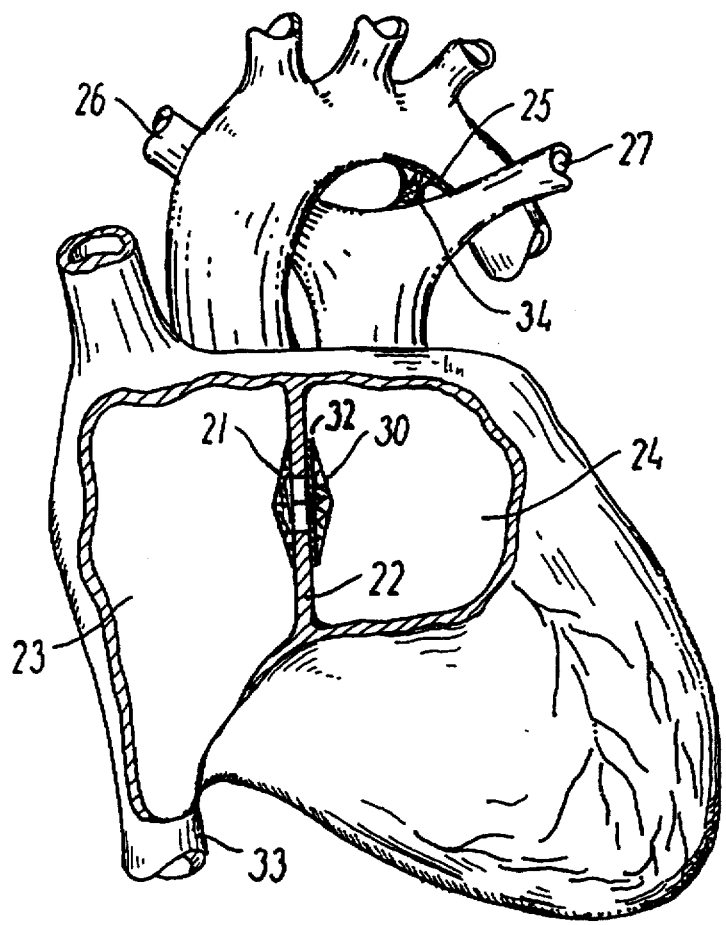
FIG. 8 illustrates the function of the embodiment shown in FIG. 6 and 7 to close socalled ASD and PDA defects in the atrial septum and between the pulmonary arteria and the aorta, respectively.

FIG. 8 illustrates schematically the application of the two latter embodiments for closing, on one hand, an ASD 21 in the septum 22 between the right and left atria 23 and 24 and on the other hand a PDA 25 forming a duct between the bifurcation of the pulmonary arteria 26 and 27 and the aorta 28 typically opposite the outlet to the subclavian arteria 29.

For the ASD closing is provided by means the above described embodiment of the occluder device composed of two bodies 30 of a pronounced flat conical or parabolic shape with relatively large diameter base ends facing each other and the elastic membrane 32. Such a device may typically be introduced from the femoral vein through the lower caval vein 33 opening into the right atrium.

For the PDA closing is provided by means of a single body device 34 as exemplified by the embodiment of FIG. 7 which may likewise be introduced through the femoral and lower caval veins.

Thus, by means of the medical article of the invention ASD and PDA defects may be cured without any need of open-heart surgery and with a considerably simpler delivery system and procedure than available in the prior art.

Figure 9:
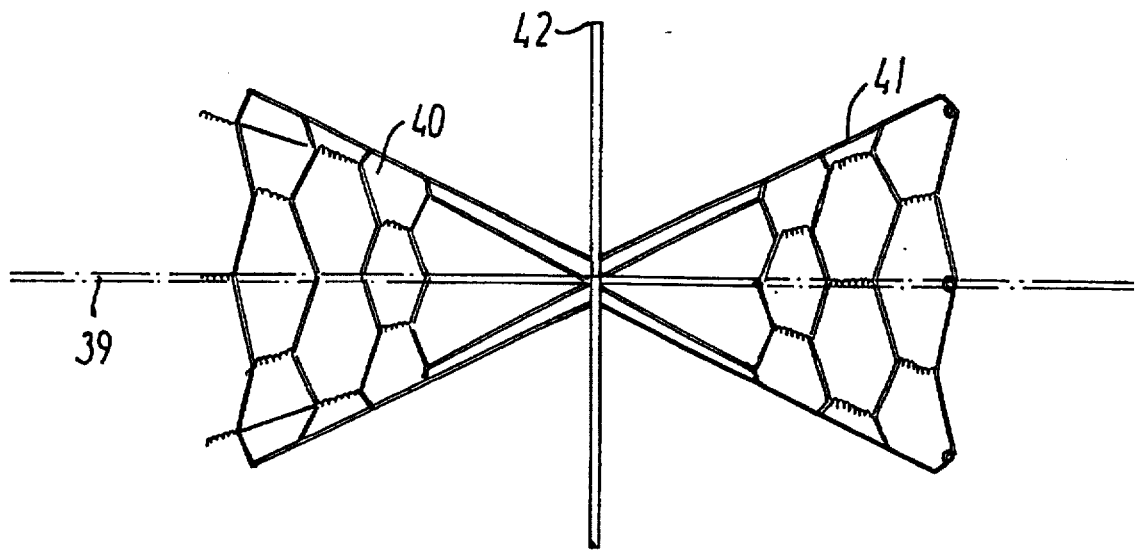
FIG. 9 is a side view of a third embodiment of the medical article of the invention.

FIG. 9 shows an embodiment specifically designed for permanent complete occlusion of a part of the venous system comprising a matricular vein section to which smaller branch veins are connected in a bifurcation or trifurcation. In its general configuration the medical article may correspond the embodiment of FIGS. 3 to 5 with the modification that an injection catheter 39 extends axially through the two bodies of revolution 40 and 41 and the elastic membrane 42 which is constructed to provides sealing around the catheter 39 and also seal-off the axial passage for the catheter after removal of the latter.

By implantation of the medical article of FIG. 9 in the matricular section of the vein complete occlusion will be provided for the downstream section thereof with which the branch veins communicate. By means of the catheter 39 it is now possible to inject an agent such as alcohol which will provide occlusion of the branch veins in the same operation.

Figure 10:
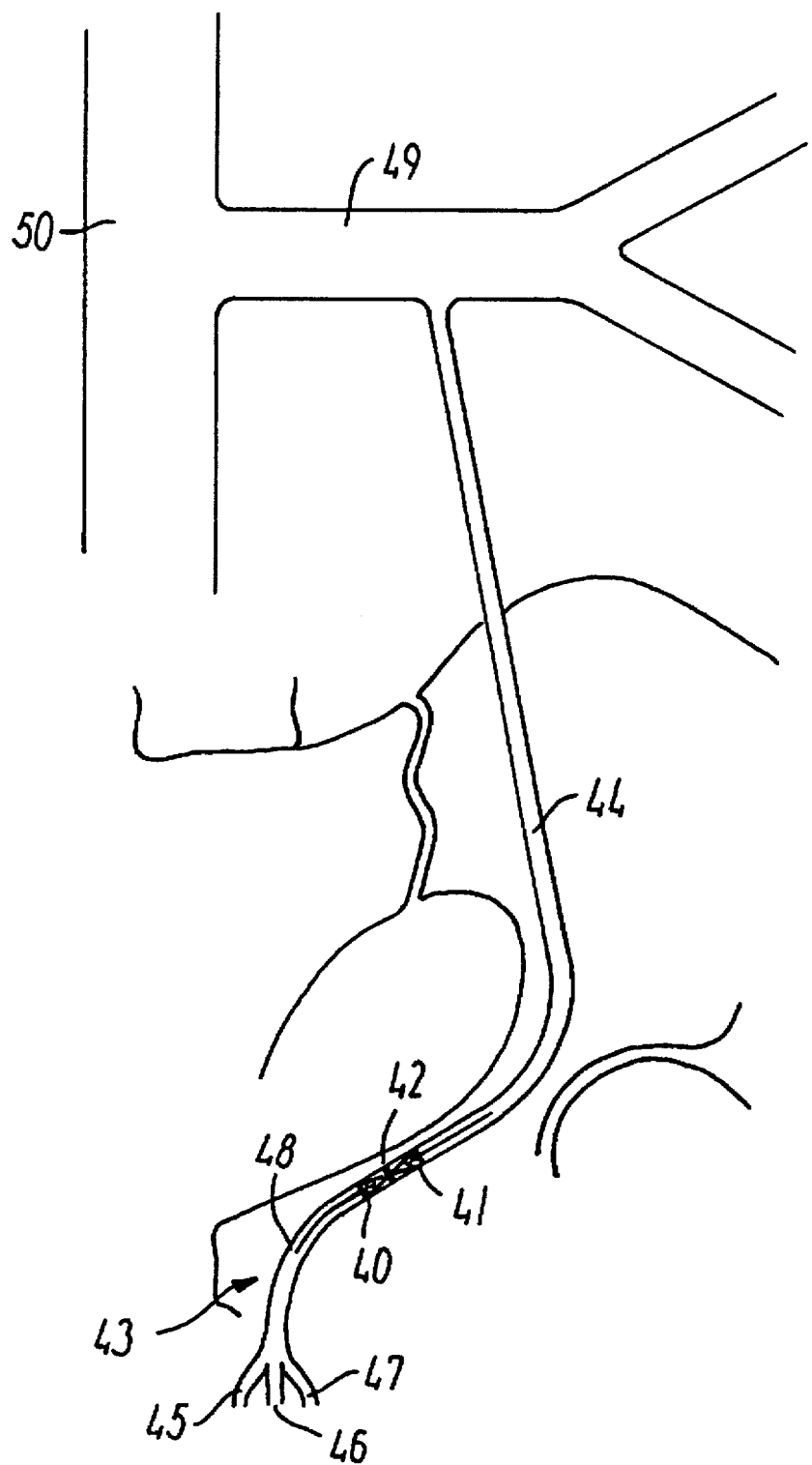
FIG. 10 illustrates application of the embodiment of FIG. 9 for complete occlusion of a lower part of the spermatic venous system.

As an example FIG. 10 illustrates application of the embodiment of FIG. 9 to the treatment of varicocele associated with the therapy of male infertility by occlusion the infrainguinal segurent 43 of the spermatic vein 44 communicating in its lower end with the complex venous drainage system of the scrotum including the pampiniform plexus and the testicular veins as schematically exemplified by the vein group 45–47 joining segurent 43 in a trifurcation. In its upper part the spermatic vein 44 communicates through the renal vein 49 with the lower caval vein 50.

As shown in FIG. 10 the article of FIG. 9 may be implanted at the level of the superficial inguinal ring 48 and after proper localization and implantation an injection of alcohol typically in an amount of about 3 ml may be administered through catheter 39 to the infrainguinal segment 43 to occlude the branch veins 45 to 47.

Whereas various embodiments of the medical article of the invention have been described hereinbefore these examples and the medical applications associated therewith should not be considered exhaustive. The invention opens for a wide range of modifications and further developments for treatment of a diversity of defects in the human vascular system within the scope of the following claims.

We claim:

1. A medical article for implantation into a blood vessel of a patient, comprising a self expanding body shaped substantially into a body of revolution, a surface of which is defined by wire members forming cells of a generally polygonal shape over at least a part of said surface, wherein said body of revolution has a diameter increasing continuously in an axial direction of the body from one end forming an apex towards a opposite end forming a base and wherein said body of revolution is defined by a generatrix forming a n-th order curve according to a formula $$y = Ax^n$$

where for a given point on the surface of the body, x is a radius in a radial plane including said point, y is a distance from said radial plane to a plane parallel thereto including a geometrical apex, A is a constant, and $n \geq 1$.

2. A medical article as claimed in claim 1 wherein said cells are of a general rhombic shape.

3. A medical article as claimed in claim 1 further comprising anchoring members for fixing the article to the walls of a blood vessel and provided at a circumference of said base.

4. A medical article as claimed in claim 1 wherein said article is provided with wire members extending substantially diametrically across said base and being connected with each at the center to function as extraction members.

5. A medical article as claimed in claim 1 wherein said article comprises first and second bodies of revolution joined at their apices.

6. A medical article as claimed in claim 5 wherein a membrane is arranged between said first and second bodies.

7. A medical article as claimed in claim 6 wherein said membrane is connected with said first and second bodies of revolution through a flexible link.

8. A medical article as claimed in claim 1 wherein said body of revolution is of a generally parabolic shape with $1 < n \leq 2$.

9. A medical article as claimed in claim 1 wherein an elastic blood impermeable membrane is arranged at one end of said body of revolution and coaxially therewith, said membrane having a diameter exceeding the maximal diameter at the base of said body.

10. A medical article as claimed in claim 9 wherein said membrane is arranged at the apex end of said body of revolution.

11. A medical article as claimed in claim 9 wherein said membrane is connected with said body of revolution through a flexible link.

12. A medical device as claimed in claim 9 wherein said membrane is a porous film or non-woven fabric of at least one of a group of polyurethane, polyethylene, polyamide, and polytetrafluoroethylene.

13. A medical article as claimed in claim 1 wherein said cells are of a generally pentagonal or hexagonal shape.

* * * * *